(12) United States Patent
Boss et al.

(10) Patent No.: US 11,580,443 B2
(45) Date of Patent: Feb. 14, 2023

(54) FACILITATING CLIENT ERGONOMIC SUPPORT VIA MACHINE LEARNING

(71) Applicant: Kyndryl, Inc., New York, NY (US)

(72) Inventors: Gregory J. Boss, Saginaw, MI (US); Zachary A. Silverstein, Austin, TX (US); Michael Bender, Rye Brook, NY (US); Jeremy R. Fox, Georgetown, TX (US)

(73) Assignee: Kyndryl, Inc., New York, NY (US)

( * ) Notice: Subject to any disclaimer, the term of this patent is extended or adjusted under 35 U.S.C. 154(b) by 915 days.

(21) Appl. No.: 16/442,300

(22) Filed: Jun. 14, 2019

(65) Prior Publication Data

US 2020/0394556 A1    Dec. 17, 2020

(51) Int. Cl.
  *G06N 20/00*   (2019.01)
  *G16H 50/20*   (2018.01)
  *H04L 67/12*   (2022.01)

(52) U.S. Cl.
  CPC .............. *G06N 20/00* (2019.01); *G16H 50/20* (2018.01); *H04L 67/12* (2013.01)

(58) Field of Classification Search
  CPC ........ G06N 20/00; G06N 5/022; G16H 50/20; G16H 20/30; H04L 67/12
  See application file for complete search history.

(56) References Cited

U.S. PATENT DOCUMENTS

| | | | |
|---|---|---|---|
| 9,855,005 B2 | 1/2018 | Cheng | |
| 10,562,412 B1* | 2/2020 | Main | A61B 5/6893 |
| 2013/0012786 A1 | 1/2013 | Horseman | |

(Continued)

FOREIGN PATENT DOCUMENTS

| | | |
|---|---|---|
| CN | 106420134 A | 2/2017 |
| KR | 20010006395 A | 1/2001 |

OTHER PUBLICATIONS

PostureScreen: Accurate Postural Assessment. PostureCo, accessed May 26, 2019. [21 printed pages] <https://www.postureanalysis.com/posturescreen-posture-movement-body-composition-analysis-assessment/>.

(Continued)

*Primary Examiner* — Kim T Nguyen
(74) *Attorney, Agent, or Firm* — The Steadman Law Firm PLLC

(57) ABSTRACT

Techniques are described with respect to facilitating client ergonomic support. An associated method includes receiving a plurality of posture datapoints associated with multiple clients and constructing a machine learning knowledge model based upon the plurality of posture datapoints in order to identify a plurality of predefined ergonomic support design elements. The method further includes receiving client-specific posture datapoints associated with a first client and analyzing, via the machine learning knowledge model, the client-specific posture datapoints in view of the plurality of posture datapoints in order to select an initial ergonomic support design element among the plurality of predefined ergonomic support design elements. The method further includes facilitate printing of the initial ergonomic support design element for a seat component associated with the first client. In an embodiment, the method further includes providing at least one ergonomic refinement to the first client based upon ergonomic sensor data.

20 Claims, 5 Drawing Sheets

(56) References Cited

U.S. PATENT DOCUMENTS

2016/0129637 A1   5/2016   Zhou et al.
2017/0311726 A1   11/2017  Danielson
2017/0325599 A1*  11/2017  Bellam .................... A47C 7/62

OTHER PUBLICATIONS

Choosing the Right Ergonomic Office Chair. spine-health.com, accessed May 26, 2019. [4 printed pages] <https://www.spine-health.com/wellness/ergonomics/office-chair-choosing-right-ergonomic-office-chair>.

Park, Mingyu et al. Design and Implementation of a smart chair system for IoT. 2016 International Conference on Information and Communication Technology Convergence (ICTC), Oct. 19-21, 2016, pp. 1200-1203.

Monash University. New smart chair technology to improve health of workers. Medical Xpress, Jun. 19, 2015. [3 printed pages] <https://medicalxpress.com/news/2015-06-smart-chair-technology-health-workers.html>.

3D Systems Unveils 3D printed Bespoke Braces for Chronic Condition Scoliosis. 3D Systems Corporation News Release, Jun. 9, 2014. [3 printed pages] <https://www.3dsystems.com/press-releases/3d-systems-unveils-3d-printed-bespoketm-braces-chronic-condition-scoliosis>.

3D Printing of Medical Devices. U.S. Food & Drug Administration, Sep. 27, 2018. [3 printed pages] <https://www.fda.gov/medical-devices/products-and-medical-procedures/3d-printing-medical-devices>.

Thomas. IKEA is using 3D printing to design ergonomic chair, the Ubik, for gamers. www.3ders.org, Sep. 11, 2018. [10 printed pages] <https://www.3ders.org/articles/20180911-ikea-is-using-3d-printing-to-design-ergonomic-chair-the-ubik-for-gamers.html>.

Horvath, P. G. et al. Body Pressure Distribution Maps Used for Sitting Comfort Visualization. SIGURNOST 59 (2), pp. 123-132, Mar. 1, 2017.

Ot, Martina Tierney. The Importance of Loading the Feet in Sitting. Seating Matters, Apr. 22, 2016. [6 printed pages] <http://blog.seatingmatters.com/3-reasons-footplate-essential>.

\* cited by examiner

FACILITATING CLIENT ERGONOMIC SUPPORT VIA MACHINE LEARNING

BACKGROUND

The various embodiments described herein generally relate to addressing client ergonomic support. More specifically, the various embodiments describe techniques of facilitating client ergonomic support via a machine learning knowledge model.

Certain individuals may need ergonomic support beyond what is provided by a given seat component. Specifically, a seat component may not adequately address posture issues and/or medical conditions associated with an individual. Additionally, a seat component may not adequately address ergonomic support at certain pressure points of an individual. Furthermore, a seat component may not adequately address respective individual preferences or needs in terms of comfort or functionality.

SUMMARY

The various embodiments described herein provide techniques of facilitating client ergonomic support via machine learning. According to an embodiment, an associated computer-implemented method includes constructing a machine learning knowledge model based upon a plurality of posture datapoints associated with multiple clients in order to identify a plurality of predefined ergonomic support design elements. The computer-implemented method further includes analyzing, via the machine learning knowledge model, client-specific posture datapoints associated with a first client in view of the plurality of posture datapoints associated with the multiple clients in order to select an initial ergonomic support design element among the plurality of predefined ergonomic support design elements. The computer-implemented method further includes facilitating printing of the initial ergonomic support design element for a seat component associated with the first client. Furthermore, the computer-implemented method includes providing at least one ergonomic refinement to the first client based upon ergonomic sensor data. Optionally, the computer-implemented method includes, responsive to detecting a change in posture of the first client via the ergonomic sensor data, notifying the first client of the change in posture via at least one alert.

In an embodiment, the step of constructing the machine learning knowledge model includes assigning to each client among the multiple clients a respective ergonomic support design category among a plurality of ergonomic support design categories and facilitating printing of a respective test ergonomic support design element for each client among the multiple clients based upon the respective ergonomic support design category assigned to the client. The step of constructing the machine learning knowledge model further includes receiving evaluation data for each client among the multiple clients based upon sensor data collected from the respective test ergonomic support design element assigned to the client and identifying one or more ergonomic patterns based upon analyzing the evaluation data in view of the plurality of posture datapoints. The step of constructing the machine learning knowledge model additionally includes training the machine learning knowledge model based upon the identified one or more ergonomic patterns and defining the plurality of predefined ergonomic support design elements based upon the trained machine learning knowledge model.

In an embodiment, one or more of the client-specific posture datapoints associated with the first client are based upon data from at least one weight sensor affixed to the seat component associated with the first client. According to such embodiment, one or more posture preferences of the first client initially may be determined consequent to data from the at least one weight sensor. In a further embodiment, the step of facilitating printing of the initial ergonomic support design element for the seat component associated with the first client includes facilitating printing of at least one armrest for the initial ergonomic support design element based upon measurements of the first client.

In an embodiment, the step of providing the at least one ergonomic refinement to the first client includes analyzing, via the machine learning knowledge model, data from a plurality of ergonomic sensors associated with the initial ergonomic support design element and updates to the plurality of posture datapoints in order to determine an additional ergonomic support design element. According to such embodiment, the step of providing the at least one ergonomic refinement further includes facilitating printing of the additional ergonomic support design element for the seat component associated with the first client. In a further embodiment, the step of providing the at least one ergonomic refinement to the first client includes transmitting to a medical professional data from a plurality of ergonomic sensors associated with the initial ergonomic support design element, receiving from the medical professional an ergonomic evaluation associated with the first client based upon the data from the plurality of ergonomic sensors, and analyzing the ergonomic evaluation in order to determine an additional ergonomic support design element. According to such further embodiment, the step of providing the at least one ergonomic refinement additionally includes facilitating printing of the additional ergonomic support design element for the seat component associated with the first client.

One or more additional embodiments pertain to a computer program product including a computer readable storage medium having program instructions embodied therewith. According to such embodiment(s), the program instructions may be executable by a computing device to cause the computing device to perform one or more steps of above recited computer-implemented method. One or more further embodiments pertain to a system having a processor and a memory storing an application program, which, when executed on the processor, performs one or more steps of the above recited computer-implemented method.

BRIEF DESCRIPTION OF THE DRAWINGS

So that the manner in which the above recited aspects are attained and can be understood in detail, a more particular description of embodiments, briefly summarized above, may be had by reference to the appended drawings.

Note, however, that the appended drawings illustrate only typical embodiments of this invention and are therefore not to be considered limiting of its scope, for the invention may admit to other equally effective embodiments.

DETAILED DESCRIPTION

Figure 1:
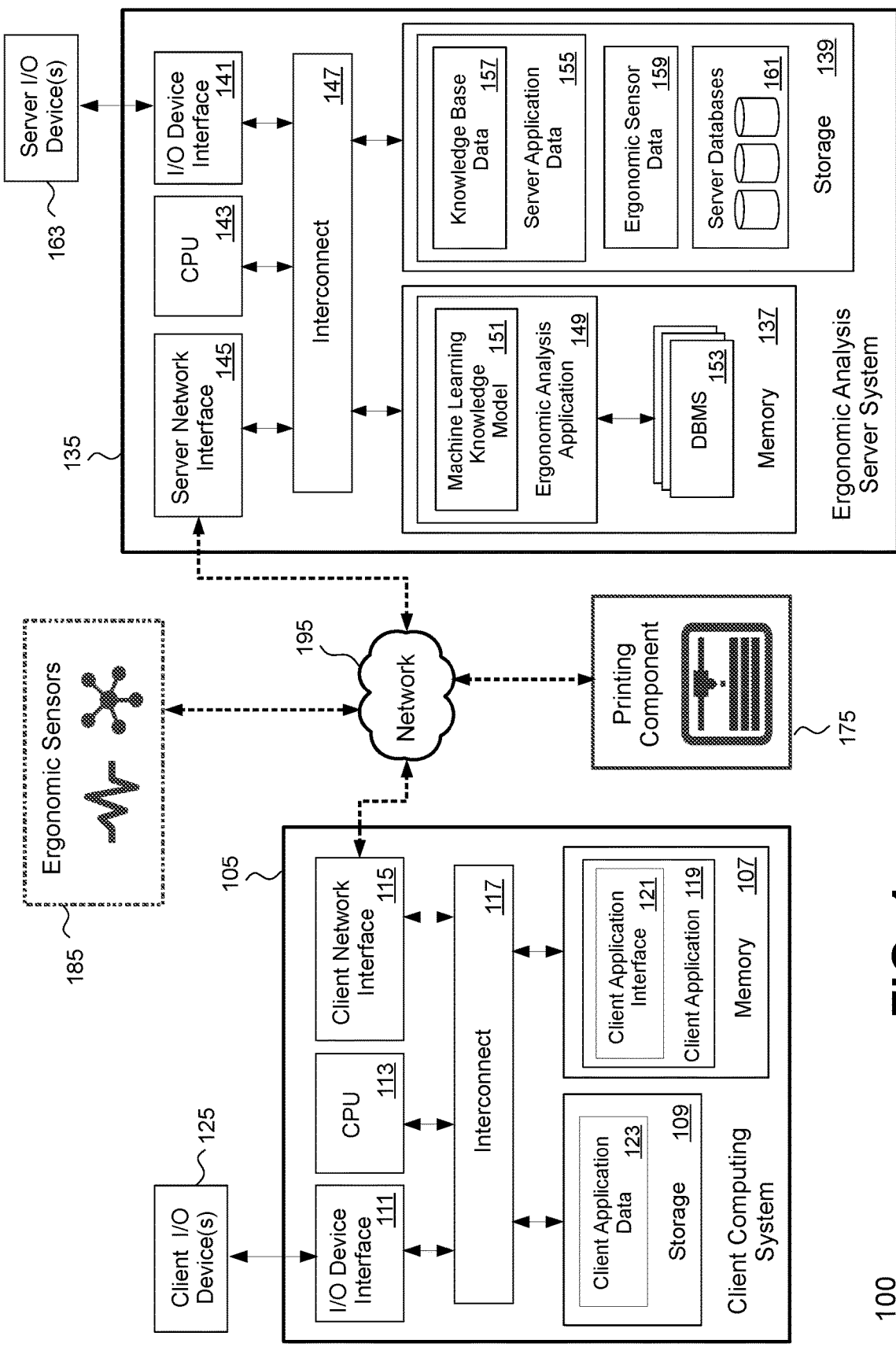
FIG. 1 illustrates a computing infrastructure, according to one or more embodiments.

The various embodiments described herein are directed to techniques of facilitating client ergonomic support via a machine learning knowledge model. An ergonomic analysis server system configured to implement techniques associated with the various embodiments described herein analyzes client ergonomic data via the machine learning knowledge model and facilitates printing of at least one ergonomic support design element based upon such analysis.

The various embodiments described herein may have advantages over conventional techniques. Specifically, the various embodiments may improve computer technology by utilizing machine learning to facilitate printing of one or more ergonomic support design elements in order to address posture issues and/or medical conditions associated with an individual client. Specifically, the various embodiments address ergonomic support at one or more pressure points of an individual client. Furthermore, the various embodiments facilitate ergonomic support in order to address any individual client preferences or needs in terms of comfort or functionality. The various embodiments optionally facilitate iterative amelioration of client ergonomic support issues by repeatedly analyzing, via machine learning and/or medical professional evaluation, ergonomic sensor data associated with an individual client and posture datapoints associated with multiple clients and facilitating printing of ergonomic support design elements in succession based upon the repeated analysis. Some of the various embodiments may not include all such advantages, and such advantages are not necessarily required of all embodiments.

In the following, reference is made to various embodiments of the invention. However, it should be understood that the invention is not limited to specific described embodiments. Instead, any combination of the following features and elements, whether related to different embodiments or not, is contemplated to implement and practice the invention. Furthermore, although embodiments may achieve advantages over other possible solutions and/or over the prior art, whether or not a particular advantage is achieved by a given embodiment is not limiting. Thus, the following aspects, features, embodiments, and advantages are merely illustrative and are not considered elements or limitations of the appended claims except where explicitly recited in a claim(s) Likewise, reference to "the invention" shall not be construed as a generalization of any inventive subject matter disclosed herein and shall not be considered to be an element or limitation of the appended claims except where explicitly recited in a claim(s).

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network, and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++, or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions also may be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions also may be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Particular embodiments describe techniques relating to facilitating client ergonomic support. However, it is to be understood that the techniques described herein may be adapted to a variety of purposes in addition to those specifically described herein. Accordingly, references to specific embodiments are included to be illustrative and not limiting.

FIG. 1 illustrates a computing infrastructure 100, according to an embodiment. As shown, computing infrastructure 100 includes a client computing system 105, an ergonomic analysis server system 135, a printing component 175, and a plurality of ergonomic sensors 185, each connected to a communications network 195.

Illustratively, client computing system 105 includes, or is otherwise operatively coupled to, a memory 107, storage 109, an input/output (I/O) device interface 111, a central processing unit (CPU) 113, and a client network interface 115, all of which are interconnected via interconnect 117 (e.g., a bus). One or more aspects of client computing system 105 are accessed or controlled by one or more clients, such as a client requesting ergonomic support. Although shown as a single computing system, client computing system 105 is included to be representative of a single client or multiple clients. In an embodiment, client computing system 105 is a thin client. Memory 107 includes a client ergonomic support application 119. Client ergonomic support application 119 may be an online application configured for interfacing with ergonomic analysis server system 135 and other computing systems. Client ergonomic support application 119 includes a client application interface 121. In the event of multiple clients, multiple instances of client computing system 105 may be present, each having a respective client ergonomic support application 119 including at least one respective client application interface 121. Client application interface 121 includes a graphical user interface (GUI), a command line interface, and/or a sensory interface (e.g., capable of discerning and processing client sound/voice commands). Storage 109 includes client application data 123 associated with client ergonomic support application 119. One or more components of a GUI, a command line interface, and/or a sensory interface included in client application interface 121 may facilitate client input and/or may facilitate display of client application data 123. I/O device interface 111 is communicatively coupled to one or more client I/O devices 125 (e.g., touchscreen console, trackpad, joystick, microphone, speaker, etc.). The client(s) may interact with client application interface(s) 121 via the one or more client I/O devices 125. CPU 113 is included to be representative of a single CPU, multiple CPUs, a single CPU having multiple processing cores, and the like. Client network interface 115 is configured to receive data from and transmit data to ergonomic analysis server system 135 via network 195.

Although shown as a single computing system, ergonomic analysis server system 135 is included to be representative of a single server system or multiple server systems. In an embodiment, ergonomic analysis server system 135 includes a single hardware server configured to provide hosting capabilities. In an alternative embodiment, ergonomic analysis server system 135 includes, or is otherwise operatively coupled to, a plurality of hardware and/or virtualized servers configured to provide hosting capabilities. In a further alternative embodiment, ergonomic analysis server system 135 is a cloud server system configured to provide distributed hosting capabilities via a plurality of cloud computing nodes in a cloud computing environment. According to such further alternative embodiment, the cloud computing nodes are configured to communicate with one another. Additionally, according to such further alternative embodiment, the cloud computing environment optionally offers infrastructure, platforms, and/or software as a service for which client computing system 105 or other systems associated with computing infrastructure 100 need not maintain resources locally.

Illustratively, ergonomic analysis server system 135 includes, or is otherwise operatively coupled to, memory 137, storage 139, an I/O device interface 141, a CPU 143, and a server network interface 145, all of which may be interconnected via interconnect 147 (e.g., a bus). Memory 137 includes an ergonomic analysis server application 149. Ergonomic analysis server application 149 includes or is otherwise operatively coupled to a machine learning knowledge model representation 151. In an embodiment, ergonomic analysis server application 149 is configured to execute one or more artificial intelligence algorithms utilizing one or more machine learning techniques via machine learning knowledge model representation 151. According to such embodiment, machine learning knowledge model representation 151 includes or is otherwise operatively coupled to a machine learning knowledge model and at least one knowledge base associated therewith. According to such embodiment, some or all aspects of the machine learning knowledge model may run within ergonomic analysis server system 135. Additionally or alternatively, some or all aspects of machine learning knowledge model may run externally to ergonomic analysis server system 135, e.g., via a cloud-based implementation, in which case ergonomic analysis server system 135 communicates with the machine learning knowledge model via machine learning knowledge model representation 151. Some or all aspects of the at least one knowledge base optionally are incorporated into ergonomic analysis server system 135. Alternatively, some or all aspects of the at least one knowledge base are externally located and communicatively coupled to ergonomic analysis server system 135. Memory 137 further includes or is otherwise operatively coupled to database management system (DBMS) 153. DBMS 153 is included to be representative of a single database system or multiple database systems. Ergonomic analysis server application 149 is configured to facilitate client ergonomic support according to the various embodiments described herein. In an embodiment, ergonomic analysis server application 149 facilitates authentication of client computing system 105 and/or other client systems in computing infrastructure 100. In an alternative embodiment, ergonomic analysis server application 149 sends authentication information associated with client computing system 105 and/or other client systems to an external directory server system, which may in turn perform any necessary authentication steps.

Storage 139 includes server application data 155. Ergonomic analysis server application 149 generates and processes server application data 155 based on interaction with other components of computing infrastructure 100. Server application data 155 includes knowledge base data 157 generated and/or used by the machine learning knowledge model. Knowledge base data 157 includes client ergonomic datapoints. In an embodiment, knowledge base data 157 includes data associated with the at least one knowledge base. Storage 139 further includes ergonomic sensor data 159 associated with (e.g., received from) the plurality of ergonomic sensors 185. Storage 139 further includes server databases 161. DBMS 153 includes or interfaces with a software application configured to manage server databases 161. In an embodiment, ergonomic analysis server application 149 sends database requests to DBMS 153 and processes results returned by DBMS 153. In a further embodiment, server databases 161 include one or more relational databases. In an additional embodiment, server databases 161 include one or more ontology trees or other ontological structures. While FIG. 1 illustrates three server databases 161, ergonomic analysis server system 135 (and more generally computing infrastructure 100) may include any number of databases. According to a further embodiment, DBMS 153 sends requests to remote databases (not shown) via network 195. I/O device interface 141 is communicatively coupled to one or more server I/O devices 163. CPU 143 is included to be representative of a single CPU, multiple CPUs, a single CPU having multiple processing cores, and the like. Server network interface 145 is configured to receive data from and transmit data to client computing system 105 or other client system(s) via network 195. Specifically, ergonomic analysis server application 149 is configured to accept requests sent by client computing system 105 or other client system(s) to ergonomic analysis server system 135 and is configured to transmit data to client computing system 105 or other client system(s) via server network interface 145. Furthermore, server network interface 145 is configured to receive data from and/or transmit data to printing component 175 and/or the plurality of ergonomic sensors 185 via network 195.

Printing component 175 is configured to print one or more ergonomic support design elements based upon input received from ergonomic analysis server system 135, more specifically ergonomic analysis server application 149. In an embodiment, printing component 175 is a three-dimensional printer or other hardware device configured to produce an ergonomic support design element. In the context of the various embodiments, an ergonomic support design element is an apparatus, a product, and/or an article of manufacture configured to supplement ergonomic support as provided by a seat component. Specifically, an ergonomic support design element is a physical (hardware) seat component attachment for placement on or around a seat component and/or a physical (hardware) seat component insert for placement within a seat component. In an embodiment, an ergonomic support design element optionally includes both a seat component attachment and a seat component insert. In the context of the various embodiments, a seat component is a chair, couch/sofa/loveseat portion, bench portion, stool, footrest, or any other physical component configured to provide ergonomic support to an individual. In the context of the various embodiments, ergonomic support refers to support for one or more spinal portions, an upper back region, a lower back/lumbar region, shoulders, a neck region, lower abdomen region, arms, legs, hands, and/or feet of an individual. In a further embodiment, one or more inner portions of an ergonomic support design element are relatively more rigid for purposes of support (e.g., use of relatively harder plastics or other materials such as fiberglass), while one or more outer portions are relatively less rigid (e.g., use of relatively softer plastics or other materials such as foam). In a further embodiment, one or more portions of an ergonomic support design element include a substrate of plastic, paper, foam, gel, and/or other material. In a further embodiment, an ergonomic support design element includes one or more apertures to facilitate airflow.

The plurality of ergonomic sensors 185 are Internet of Things (IoT) sensors capable of communicating with other systems or devices in computing infrastructure 100, including client computing system 105, ergonomic analysis server system 135, and/or printing component 175. In an embodiment, the plurality of ergonomic sensors 185 include analog sensors and/or digital sensors. One or more sensors among the plurality of ergonomic sensors 185 optionally include both analog and digital characteristics. In a further embodiment, one or more of the plurality of ergonomic sensors 185 are located on or are otherwise attached to an ergonomic support design element printed by printing component 175. Additionally or alternatively, one or more of the plurality of ergonomic sensors 185 are otherwise operatively coupled with or associated with an ergonomic support design element printed by printing component 175.

Figure 2:
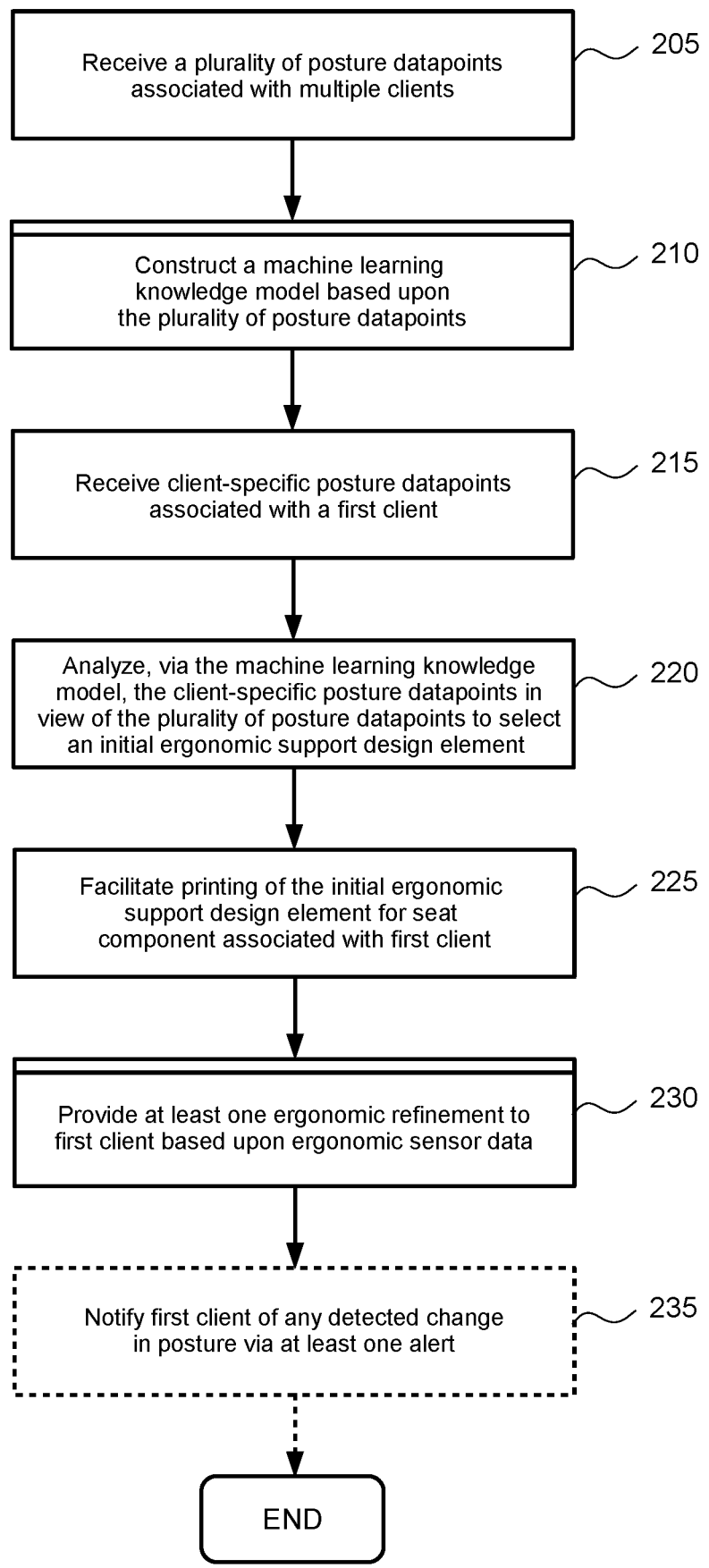
FIG. 2 illustrates a method of facilitating client ergonomic support, according to one or more embodiments.

FIG. 2 illustrates a method 200 of facilitating client ergonomic support. One or more steps associated with the method 200 and the other methods described herein may be carried out in a client-server computing environment (e.g., computing infrastructure 100) including a network (e.g., network 195). An ergonomic analysis application in an ergonomic analysis server system of the client-server computing environment (e.g., ergonomic analysis server application 149 in ergonomic analysis server system 135 of computing infrastructure 100) facilitates processing according to the method 200 and the other methods further described herein. The ergonomic analysis application interacts with each of one or more clients via a respective client interface associated with a client ergonomic support application of a client computing system (e.g., client application interface 121 associated with client ergonomic support application 119 of client computing system 105). Additionally or alternatively to the client-server computing environment, one or more steps associated with the method 200 and the other methods described herein may be carried out within one or more workloads of a cloud computing environment. Additionally or alternatively, one or more steps associated with the method 200 and the other methods described herein may be carried out in a peer-to-peer network environment, in which case one or more of the method steps described herein may be carried out via a peer application of a peer computing system.

The method 200 begins at step 205, where the ergonomic analysis application receives a plurality of posture datapoints associated with multiple clients. The ergonomic analysis application optionally receives the plurality of posture datapoints via the network. In an embodiment, the plurality of posture datapoints are based upon design specifications, image(s), and/or blueprint(s) of respective seat components associated with the multiple clients. Additionally or alternatively, the plurality of posture datapoints are based upon medical information associated with the multiple clients. The medical information optionally includes medical scans associated with each of the multiple clients or a subset of the multiple clients. Such medical scans may include machine-based scans such as x-rays and/or computed tomography (CT) scans. Such medical scans further may include personal mobile scans related to posture or internal medical issues that may influence ergonomic needs. The personal mobile scans optionally are conducted via respective mobile devices of one or more of the multiple clients. Furthermore, the medical information optionally includes results of medical professional assessments performed on each of the multiple clients or a subset of the multiple clients. The results of the medical professional assessments optionally include evaluation information or test results from respective client office or clinic visits. Additionally or alternatively, the results of the medical professional assessments optionally include evaluation information or test results from respective client appointments conducted remotely, e.g., via telecommunication or teleconferencing.

In an embodiment, the ergonomic analysis application receives the plurality of posture datapoints associated with the multiple clients by querying a dataset associated with multiple clients seeking ergonomic support or otherwise contributing ergonomic data, e.g., available via one or more databases or other accessible data structures. In a further embodiment, the ergonomic analysis application applies natural language processing (NLP) to data related to each of the multiple clients or a subset of the multiple clients to determine various ergonomic pressure point characteristics among the multiple clients. To complete a NLP-related task in the context of the various embodiments described herein, the ergonomic analysis application optionally initiates or otherwise facilitates an application programming interface (API) call to an application having natural language processing capabilities, e.g., a local NLP application associated with the ergonomic analysis server system and/or a cloud-based NLP application. The ergonomic analysis application provides each of the multiple clients advance notice of any personal data collection with respect to the plurality of posture datapoints or other ergonomic aspects. The ergonomic analysis application further provides each of the multiple clients an option to opt in or opt out of any such personal data collection at any time. Optionally, the ergonomic analysis application further transmits at least one notification to any affected client each time any such personal data collection occurs.

At step 210, the ergonomic analysis application constructs a machine learning knowledge model based upon the plurality of posture datapoints associated with the multiple clients in order to identify a plurality of predefined ergonomic support design elements. Each of the plurality of predefined ergonomic support design elements is a physical seat component attachment configured for placement on/around a seat component or a physical seat component insert configured for placement within a seat component. In an embodiment, one or more of the plurality of predefined ergonomic support design elements optionally include both a seat component attachment and a seat component insert. A method with regard to constructing the machine learning knowledge model in accordance with step 210 is described with respect to FIG. 3.

At step 215, the ergonomic analysis application receives client-specific posture datapoints associated with a first client. The ergonomic analysis application optionally receives one or more of the client-specific posture datapoints, including medical information or information regarding a seat component associated with the first client for which ergonomic support is needed, directly from the first client. The first client optionally requests an ergonomic support analysis by submitting an inquiry to the ergonomic analysis server system via a respective client interface associated with a client ergonomic support application of a computing system associated with the first client, i.e., a first client interface. The first client interface optionally includes a GUI interface enabling the first client to submit one or more survey responses with respect to past or current ergonomic issues and/or enabling the first client to submit identifying information and/or information regarding the seat component. The ergonomic analysis application optionally transmits one or more survey questions to the first client via a GUI-based webpage. Such GUI-based webpage optionally includes one or more control elements, such as radio buttons, drop-down boxes, check boxes, etc., to facilitate survey response selection. Additionally or alternatively, based upon information provided with regard to the first client, the ergonomic analysis application optionally requests and receives one or more of the client-specific posture datapoints from other sources, including one or more cloud-based medical databases, one or more social media profiles, or other accessible data structures.

In an embodiment, the ergonomic analysis application receives one or more of the client-specific posture datapoints associated with the first client by receiving data from at least one weight sensor affixed to the seat component associated with the first client. According to such embodiment, one or more of the client-specific posture datapoints are based upon data from the at least one weight sensor. In a further embodiment, the ergonomic analysis application receives one or more of the client-specific posture datapoints associated with the first client by receiving image data or audiovisual data from at least one photographic sensor, e.g., associated with at least one camera monitor configured to capture at least one image and/or at least one video feed of the seat component. Based upon the data received from the at least one weight sensor and/or from the at least one photographic sensor, the ergonomic analysis application determines one or more initial posture preferences of the first client. In a further embodiment, the ergonomic analysis application applies NLP to datapoints provided by the first client and/or datapoints obtained from other sources to derive one or more further client-specific posture datapoints, e.g., one or more ergonomic pressure points associated with the first client.

In an embodiment, the client-specific posture datapoints received or otherwise processed at step 215 are based upon design specifications, image(s), and/or blueprint(s) of the seat component associated with the first client. Additionally or alternatively, the client-specific posture datapoints are based upon medical information received for the first client. First client medical information may include medical scans and/or results of medical professional assessments analogous or complementary to those previously discussed with respect to the plurality of posture datapoints associated with the multiple clients. More specifically, such medical scans may include machine-based scans such as x-rays and/or CT scans and further may include personal mobile scans optionally conducted via a mobile device of the first client. The results of medical professional assessments optionally include evaluation information or test results from first client office/clinic visits and/or evaluation information or test results from first client appointments conducted remotely, e.g., via telecommunication or teleconferencing. In a further embodiment, the ergonomic analysis application applies natural language processing (NLP) to data related to the first client to determine various ergonomic pressure point characteristics of the first client. The ergonomic analysis application provides the first client advance notice of any personal data collection with respect to the plurality of client-specific posture datapoints or other ergonomic aspects. The ergonomic analysis application further provides the first client an option to opt in or opt out of any such personal data collection at any time. Optionally, the ergonomic analysis application further transmits at least one notification to the first client each time any such personal data collection occurs.

At step 220, the ergonomic analysis application analyzes, via the machine learning knowledge model constructed at step 210, the client-specific posture datapoints in view of the plurality of posture datapoints associated with the multiple clients in order to select an initial ergonomic support design element among the plurality of predefined ergonomic support design elements. In an embodiment, the ergonomic analysis application applies machine learning to medical information associated with the first client (including scans, ergonomic medical issues, etc.) and/or information regarding the seat component associated with the first client in view of analogous or otherwise related information from the plurality of posture datapoints associated with the multiple clients. In a further embodiment, the ergonomic analysis application selects the initial ergonomic support design element that provides lumbar support to the first client and that fits the spine curvature of the first client. In a further embodiment, the ergonomic analysis application selects the initial ergonomic support design element such that a width metric of the initial ergonomic support design element is less than a width metric of the seat component associated with the first client.

In an embodiment, the ergonomic analysis application analyzes first client ergonomic input in conjunction with objective ergonomic support data in the context of selecting the initial ergonomic design element (and/or any additionally determined ergonomic design element). According to such embodiment, the ergonomic analysis application optionally obtains first client ergonomic input based upon explicit input provided via the first client interface, e.g., survey responses from the first client with respect to reclining position, typical weight distribution, etc. Additionally or alternatively, the ergonomic analysis application optionally receives datapoints related to position of the first client within the seat component over time. In a further embodiment, the ergonomic analysis application analyzes one or more seating objectives of the first client in the context of selecting the initial ergonomic design element (and/or any additionally determined ergonomic design element). For instance, the ergonomic analysis application may determine one or more motives of the first client with respect to the seat component, i.e., whether the seat component has been used, is used, and/or is to be used by the first client for business, entertainment, respite, sleep, or a combination thereof.

At step 225, the ergonomic analysis application facilitates printing of the initial ergonomic support design element for the seat component associated with the first client. In an embodiment, the ergonomic analysis application facilitates printing of the initial ergonomic support design element by transmitting a print request to a printing component (e.g., printing component 175). According to such embodiment, the printing component optionally is a three-dimensional printer or alternatively is another device capable of manufacturing, constructing, or otherwise producing the initial ergonomic support design element. In a further embodiment, the ergonomic analysis application facilitates printing of the initial ergonomic support design element by facilitating printing of at least one armrest for the initial ergonomic support design element based upon arm, elbow, wrist, and/or hand measurements of the first client. Optionally, the ergonomic analysis application schedules or otherwise facilitates a delivery of the printed initial ergonomic support element to the first client in response to first client delivery input. The first client delivery input optionally includes submission of a delivery request document via the first client interface and/or submission of a vocal delivery request via the first client interface.

At step 230, the ergonomic analysis application provides at least one ergonomic refinement to the first client based upon ergonomic sensor data. In an embodiment, the ergonomic sensor data includes data from Internet of Things (IoT) ergonomic sensors connected to the network. The ergonomic analysis application optionally receives the ergonomic sensor data via the network or alternatively via a dedicated connection between the ergonomic sensors and the ergonomic analysis application. The ergonomic sensors include sensors embedded in the initial ergonomic support design element (or any additional ergonomic support design element). The embedded sensors record pressure point data and/or body position data (e.g., spinal tilt) based upon magnitude of detected contact of the first client upon each sensor. The ergonomic sensors determine posture metrics and optionally comfort metrics based upon spinal pressure, body tilt, frequency of first client movement on the seat component, and/or frequency of first client departure from the seat component. The ergonomic sensors optionally further include peripheral sensors to record first client posture. Such peripheral sensors optionally include at least one footrest sensor. Furthermore, such peripheral sensors optionally include sensors embedded in or otherwise related to the seat component associated with the first client, including the at least one weight sensor and/or the at least one photographic sensor associated with the at least one camera monitor discussed with respect to step 215. In a further embodiment, the ergonomic analysis application provides at least one ergonomic refinement to the first client based upon medical professional observations of the first client and/or medical scans performed on the first client in addition to the ergonomic sensor data. Methods with regard to providing the at least one ergonomic refinement to the first client in accordance with step 230 are described with respect to FIG. 4 and FIG. 5.

In an embodiment, the ergonomic analysis application provides at least one ergonomic refinement to the first client in accordance with step 230 upon expiration of a predefined evaluation period with respect to the initial ergonomic support design element. Additionally or alternatively, the ergonomic analysis application provides at least one ergonomic refinement to the first client responsive to determining that a spinal pressure metric as derived from ergonomic sensor data exceeds a predefined spinal pressure threshold. Such spinal pressure metric optionally is calculated by a summation of spinal measurements from ergonomic sensors associated with the initial ergonomic support design element (or any additional ergonomic support design element). Additionally or alternatively, the ergonomic analysis application provides at least one ergonomic refinement to the first client responsive to a refinement request received from the first client, e.g., via the first client interface. A refinement request optionally includes any information regarding discomfort experienced by the first client consequent to use of the initial ergonomic support design element (or any additional ergonomic support design element). The ergonomic analysis application optionally facilitates completion of a refinement request by providing one or more survey questions to the first client via the first client interface.

Optionally, at step 235, responsive to detecting a change in posture of the first client via the ergonomic sensor data, the ergonomic analysis application notifies the first client of the change in posture via at least one alert. In an embodiment, the ergonomic analysis application detects a change in first client posture based upon a deviation beyond an expected pressure point value range in pressure point readings of one or more ergonomic sensors. The ergonomic analysis application optionally determines the expected pressure point value range based upon first client posture information. In a further embodiment, the ergonomic analysis application detects a change in first client posture via one or more images or a video feed captured by the at least one camera monitor. In a further embodiment, the ergonomic analysis application notifies the first client of the change in posture by issuing a vibration signal. According to such further embodiment, the ergonomic analysis application issues a vibration signal to any ergonomic sensor associated with the initial ergonomic support design element (or any additional ergonomic support design element) through which the ergonomic analysis application detects the change in posture. Additionally or alternatively, the ergonomic analysis application issues a vibration signal to any portion of the initial ergonomic support design element (or any additional ergonomic support design element) within which the ergonomic analysis application detects the change in posture. Additionally or alternatively, the ergonomic analysis application issues a vibration signal to a device or other component (e.g., footrest) associated with the first client. In a further embodiment, the ergonomic analysis application notifies the first client of the change in posture by transmitting a message to the first client interface. In a further embodiment, the ergonomic analysis application notifies the first client of the change in posture by issuing a text message and/or by issuing an audio based and/or video based alert to an interface component (e.g., a message display component) attached to or otherwise associated with the initial ergonomic support design element (or any additional ergonomic support design element).

Figure 3:
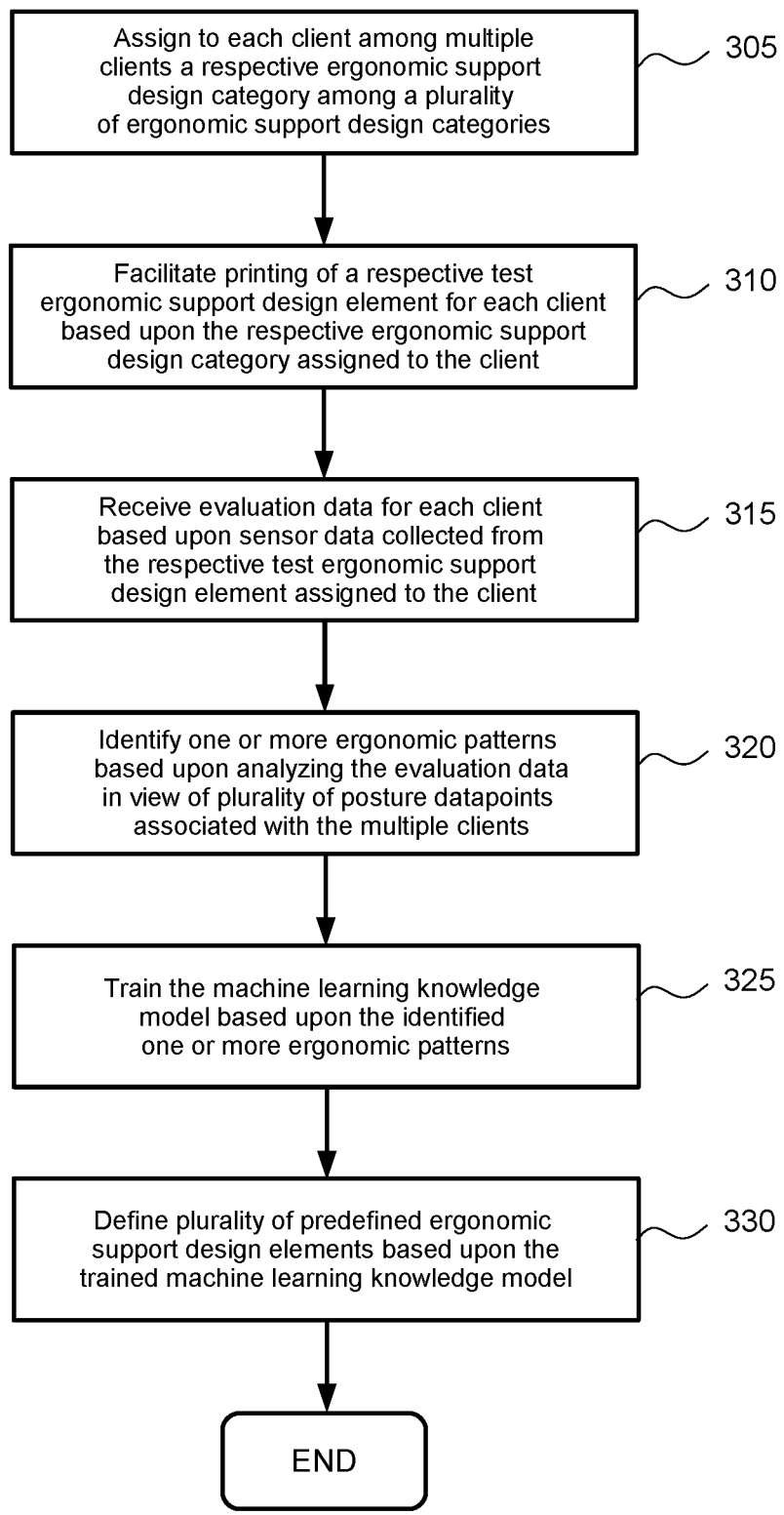
FIG. 3 illustrates a method of constructing a machine learning knowledge model associated with client ergonomic support, according to one or more embodiments.

FIG. 3 illustrates a method 300 of constructing the machine learning knowledge model based upon the plurality of posture datapoints associated with the multiple clients in order to identify the plurality of predefined ergonomic support design elements. The method 300 provides one or more example embodiments with respect to step 210 of the method 200. The method 300 begins at step 305, where the ergonomic analysis application assigns to each client among the multiple clients a respective ergonomic support design category among a plurality of ergonomic support design categories. In an embodiment, the ergonomic analysis application randomly assigns each client to a respective ergonomic support design category, e.g., based upon output from a random number generator device. Alternatively, the ergonomic analysis application assigns each client to a respective ergonomic support design category based upon posture profile data associated with the client. According to such alternative, the ergonomic analysis application maps each client to a respective ergonomic support design category based upon relative similarity between aspects of the posture profile data associated with the client and ergonomic aspects of the category. According to such alternative, the ergonomic analysis application optionally determines such client-category mappings via a quantitative analysis based upon comparison of similarity level values respectively assigned to each client-category pair. At step 310, the ergonomic analysis application facilitates printing of a respective test ergonomic support design element for each client among the multiple clients based upon the respective ergonomic support design category assigned to the client. In an embodiment, the ergonomic analysis application facilitates printing according to step 310 by transmitting one or more print requests to the printing component.

At step 315, the ergonomic analysis application receives evaluation data for each client among the multiple clients based upon sensor data collected from the respective test ergonomic support design element assigned to the client. In an embodiment, the ergonomic analysis application collects sensor data for each client according to step 315 based upon a plurality of ergonomic sensors embedded or otherwise associated with the respective test ergonomic support design element assigned to the client. At step 320, the ergonomic analysis application identifies one or more ergonomic patterns based upon analyzing the evaluation data in view of the plurality of posture datapoints associated with the multiple clients. In an embodiment, the ergonomic analysis application applies a clustering algorithm to the evaluation data in order to identify the one or more ergonomic patterns. Through application of a clustering algorithm, the ergonomic analysis application identifies patterns with respect to one or more subsets of clients among the multiple clients having common ergonomic symptoms reflected in sensor datapoints within the evaluation data. For instance, the ergonomic analysis application may identify common characteristics among a subset of clients exhibiting lower back issues based upon lower back sensor datapoints within the evaluation data. In a further embodiment, the ergonomic analysis application identifies the one or more ergonomic patterns based upon pressure point weight distribution data, pelvic tilt data, and/or head balance data within the evaluation data as derived from client sensor readings. At step 325, the ergonomic analysis application trains the machine learning knowledge model based upon the identified one or more ergonomic patterns. According to step 325, the ergonomic analysis application applies machine learning to the identified one or more ergonomic patterns to train the machine learning knowledge model. In an embodiment, the ergonomic analysis application applies machine learning according to step 325 by mapping features of the machine learning knowledge model to the identified one or more ergonomic patterns. At step 330, the ergonomic analysis application defines the plurality of predefined ergonomic support design elements based upon the trained machine learning knowledge model.

Figure 4:
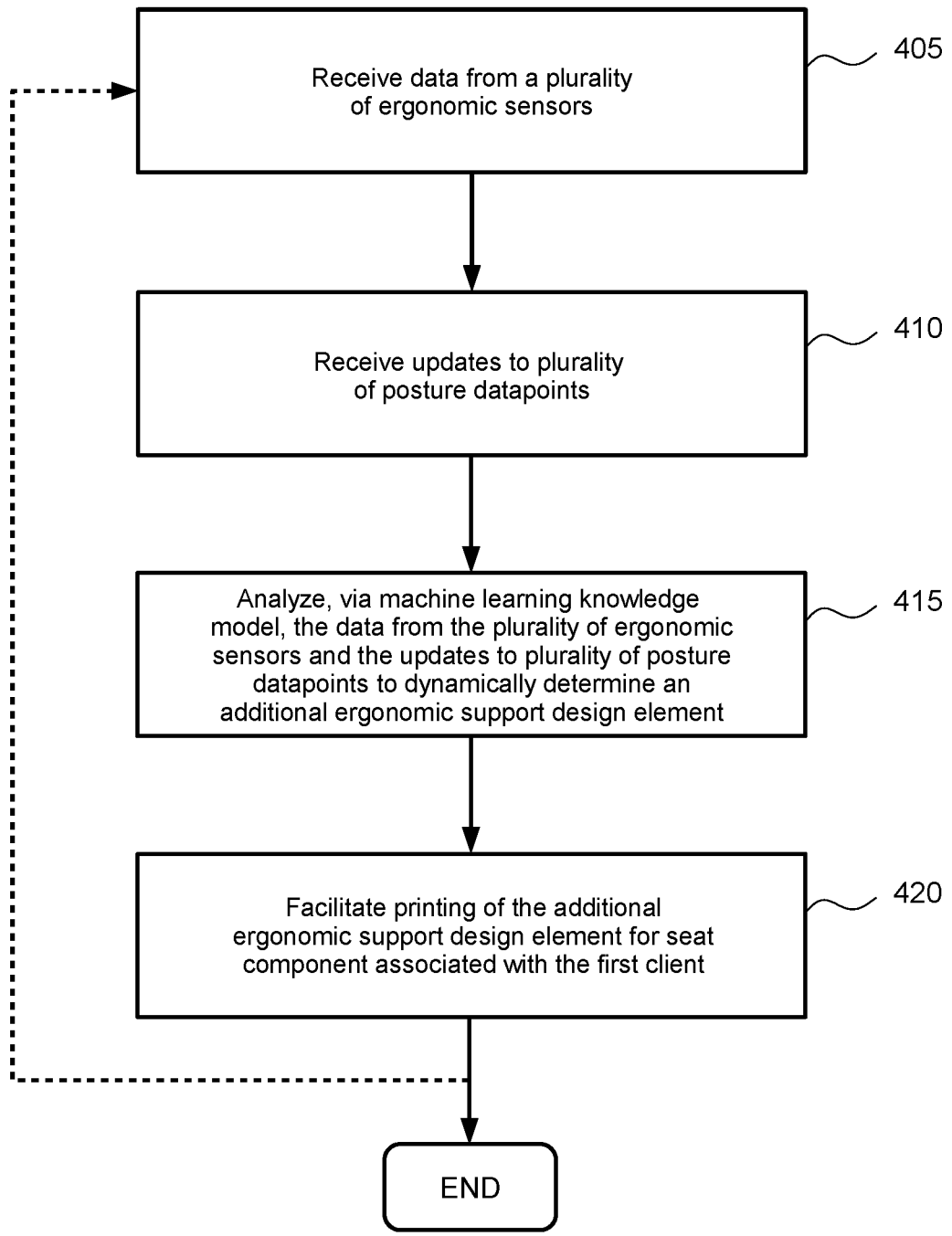
FIG. 4 illustrates a method of providing at least one client ergonomic refinement based upon ergonomic sensor data, according to one or more embodiments.

FIG. 4 illustrates a method 400 of providing at least one ergonomic refinement to the first client based upon ergonomic sensor data. The method 400 provides one or more example embodiments with respect to step 230 of the method 200. The method 400 begins at step 405, where the ergonomic analysis application receives data from a plurality of ergonomic sensors associated with the initial ergonomic support design element. Some or all of the plurality of ergonomic sensors are embedded in the initial ergonomic support design element at one or more pressure points of contact between the first client and the initial ergonomic support design element. The plurality of ergonomic sensors record first client position with respect to the initial ergonomic support design element based upon first client body position relative to the one or more pressure points of contact. Optionally, the plurality of ergonomic sensors further include peripheral sensors (e.g., at least one footrest sensor, at least one weight sensor, and/or at least one photographic sensor as discussed with respect to the method 200) to record or otherwise capture first client posture with respect to the initial ergonomic support element. The plurality of ergonomic sensors optionally determine pressure point weight distribution indicating whether equal pressure is applied by the first client at each of the one or more pressure points of contact. Additionally or alternatively, the plurality of ergonomic sensors optionally determine pelvic tilt of the first client and/or head balance of the first client. At step 410, the ergonomic analysis application receives updates to the plurality of posture datapoints associated with the multiple clients. The updates to the plurality of posture datapoints may provide ergonomic insight that was unavailable upon selection of the initial ergonomic design element according to step 220. For instance, the updates to the plurality of posture datapoints may include newly obtained information from one or more clients experiencing spinal issues that may be relevant with respect to spinal issues experienced by the first client.

At step 415, the ergonomic analysis application analyzes, via the machine learning knowledge model, the data from the plurality of ergonomic sensors associated with the initial ergonomic support design element and the updates to the plurality of posture datapoints associated with the multiple clients in order to determine (e.g., dynamically determine in real time) an additional ergonomic support design element. The ergonomic analysis application analyzes, via the machine learning knowledge model, the data from the plurality of ergonomic sensors and the updates to the plurality of posture datapoints in view of already existing information in the trained model (i.e., the plurality of posture datapoints and the client-specific posture datapoints previously received). In an embodiment, the ergonomic analysis application determines the additional ergonomic support design element at step 415 through selection among the plurality of predefined ergonomic support design elements. In an alternative embodiment, the ergonomic analysis application determines the additional ergonomic support design element at step 415 by identifying one or more modifications to one or more portions of the initial ergonomic support design element. According to such alternative embodiment, the additional ergonomic support design element is a newly created ergonomic element based upon the identified one or more modifications. Furthermore, according to such alternative embodiment, the ergonomic analysis application optionally adds such newly created ergonomic support design element to the plurality of predefined ergonomic support design elements. In a further embodiment, based upon the machine learning knowledge model analysis, the ergonomic analysis application determines the additional ergonomic support design element such that weight of the first client is shifted by the additional ergonomic support design element relative to the initial ergonomic support design element in order to increase or decrease pressure point impact. In a further embodiment, based upon the machine learning knowledge model analysis, the ergonomic analysis application determines the additional ergonomic support design element such that a shape (e.g., an angle of curvature) of at least one portion of the additional ergonomic support design element is modified relative to the initial ergonomic support design element. By increasing or decreasing pressure point impact and/or by modifying portion shape, the additional ergonomic support design element may enhance posture and/or comfort of the first client.

At step 420, the ergonomic analysis application facilitates printing of the additional ergonomic support design element for the seat component associated with the first client. In an embodiment, the ergonomic analysis application facilitates printing of the additional ergonomic support element according to step 420 by transmitting one or more print requests to the printing component. In a further embodiment, the ergonomic analysis application facilitates printing of at least one armrest for the additional ergonomic support design element according to step 420 based upon arm, elbow, wrist, and/or hand measurements of the first client. Optionally, the ergonomic analysis application schedules or otherwise facilitates a delivery of the printed additional ergonomic support element to the first client in response to first client delivery input, e.g., submission of a delivery request document and/or submission of a vocal delivery request via the first client interface.

Optionally, upon completion of the steps of the method 400, as illustrated by the broken line in FIG. 4 the ergonomic analysis application returns to step 405 to repeat the steps of the method 400 using a plurality of ergonomic sensors associated with the additional ergonomic support design element in order to determine (e.g., dynamically determine in real time) at least one further additional ergonomic support design element. More specifically, the ergonomic analysis application optionally receives data from the plurality of ergonomic sensors associated with the additional ergonomic support design element, receives additional updates to the plurality of posture datapoints associated with the multiple clients, analyzes via the machine learning knowledge model the data from the plurality of ergonomic sensors associated with the additional ergonomic design element and the additional updates to the plurality of posture datapoints in order to determine a further additional ergonomic support design element, and facilitates printing of the further additional ergonomic support design element for the seat component associated with the first client. Accordingly, execution of the steps of the method 400 and repetition thereof reflect an iterative ergonomic support design analysis technique. Accordingly, the ergonomic analysis application is configured to facilitate printing of at least one additional ergonomic support design element based upon iterative analysis of ergonomic sensor data as well as updates to the plurality of posture datapoints.

Figure 5:
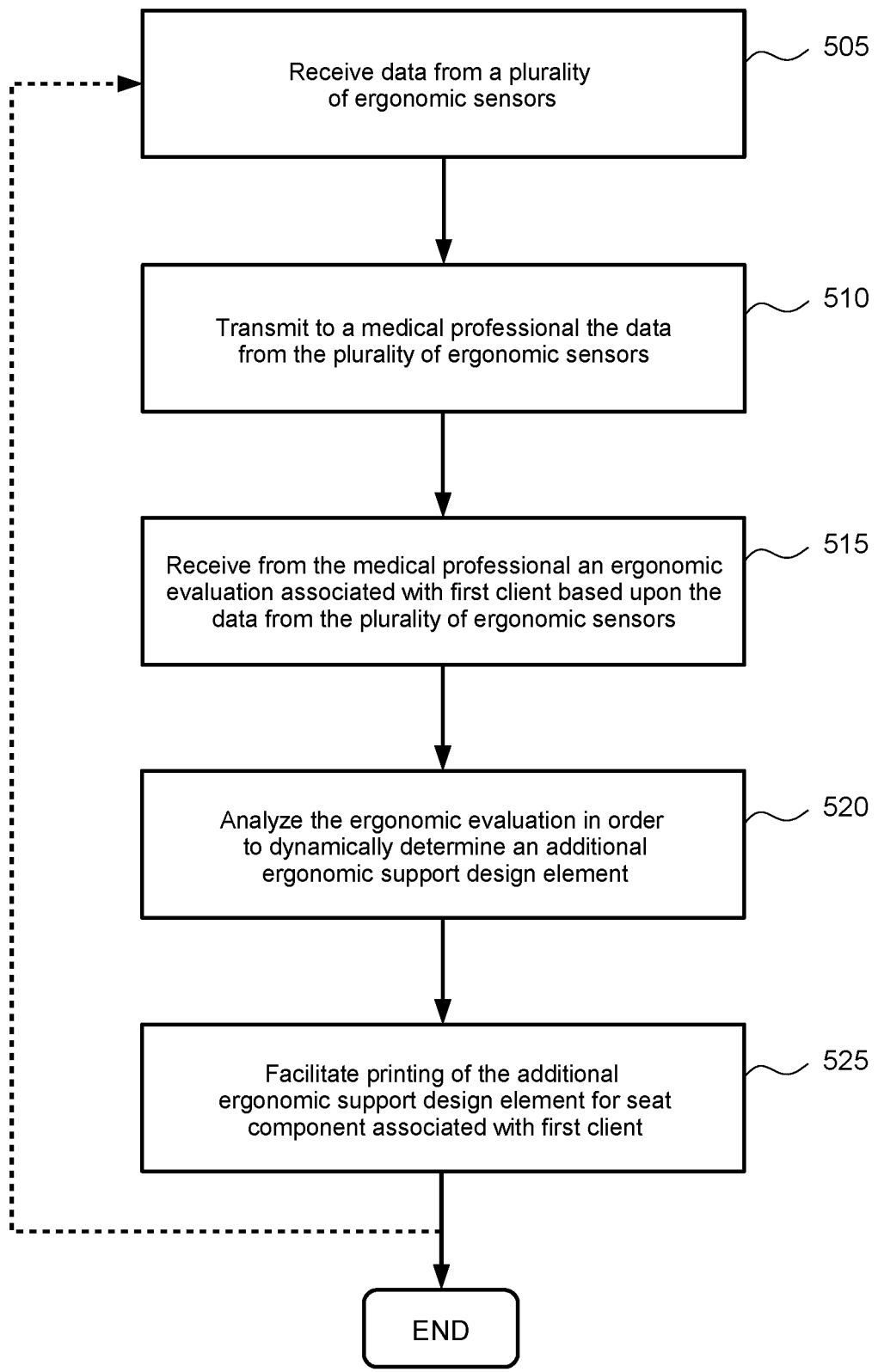
FIG. 5 illustrates a method of providing at least one client ergonomic refinement based upon ergonomic sensor data, according to one or more further embodiments.

FIG. 5 illustrates a method 500 of providing at least one ergonomic refinement to the first client based upon ergonomic sensor data. The method 500 provides one or more further example embodiments with respect to step 230 of the method 200. The method 500 begins at step 505, where the ergonomic analysis application receives data from a plurality of ergonomic sensors associated with the initial ergonomic support design element. The plurality of ergonomic sensors received at step 505 optionally are similar or identical to the plurality of ergonomic sensors previously described with respect to the method 400. At step 510, the ergonomic analysis application transmits to a medical professional the data from the plurality of ergonomic sensors. Upon receipt of the sensor data from the ergonomic analysis application, the medical professional analyzes the sensor data based upon his or her expertise. In an embodiment, the medical professional further analyzes subjective comfort level information submitted by the first client, e.g., in response to survey questions. At step 515, the ergonomic analysis application receives from the medical professional an ergonomic evaluation associated with the first client based upon the data from the plurality of ergonomic sensors (and optionally based upon subjective comfort level information submitted by the first client). In an embodiment, the ergonomic evaluation includes one or more design modifications to the initial ergonomic support design element recommended by the medical professional based upon analysis of the ergonomic sensor data. According to such embodiment, the ergonomic analysis application optionally provides to the medical professional access to the plurality of predefined ergonomic support design elements (e.g., by transmitting descriptions thereof upon transmission of the sensor data at step 510) such that the medical professional has an option to include in the ergonomic evaluation a recommendation indicating which of the plurality of predefined ergonomic support design elements is most appropriate for the first client.

At step 520, the ergonomic analysis application analyzes the ergonomic evaluation in order to determine (e.g., dynamically determine in real time) an additional ergonomic support design element. In an embodiment, the ergonomic analysis application determines the additional ergonomic support design element at step 520 through selection among the plurality of predefined ergonomic support design elements. According to such embodiment, in the event that the ergonomic evaluation includes a recommendation indicating which of the plurality of predefined ergonomic support design elements is most appropriate for the first client, the ergonomic analysis application optionally selects the recommended predefined ergonomic support design element. In an alternative embodiment, the ergonomic analysis application determines the additional ergonomic support design element at step 520 by identifying one or more modifications to one or more portions of the initial ergonomic support design element. According to such alternative embodiment, the additional ergonomic support design element is a newly created ergonomic element based upon the identified one or more modifications. Furthermore, according to such alternative embodiment, the ergonomic analysis application optionally adds such newly created ergonomic support design element to the plurality of predefined ergonomic support design elements. In a further embodiment, based upon the ergonomic evaluation analysis, the ergonomic analysis application determines the additional ergonomic support design element such that weight of the first client is shifted by the additional ergonomic support design element relative to the initial ergonomic support design element in order to increase or decrease pressure point impact. In a further embodiment, based upon the ergonomic evaluation analysis, the ergonomic analysis application determines the additional ergonomic support design element such that a shape (e.g., an angle of curvature) of at least one portion of the additional ergonomic support design element is modified relative to the initial ergonomic support design element.

At step 525, the ergonomic analysis application facilitates printing of the additional ergonomic support design element for the seat component associated with the first client. In an embodiment, the ergonomic analysis application facilitates printing of the additional ergonomic support element according to step 525 by transmitting one or more print requests to the printing component. In a further embodiment, the ergonomic analysis application facilitates printing of at least one armrest for the additional ergonomic support design element according to step 525 based upon arm, elbow, wrist, and/or hand measurements of the first client. Optionally, the ergonomic analysis application schedules or otherwise facilitates a delivery of the printed additional ergonomic support element to the first client in response to first client delivery input, e.g., submission of a delivery request document and/or submission of a vocal delivery request via the first client interface.

Optionally, upon completion of the steps of the method 500, as illustrated by the broken line in FIG. 5 the ergonomic analysis application returns to step 505 to repeat the steps of the method 500 using a plurality of ergonomic sensors associated with the additional ergonomic support design element in order to determine (e.g., dynamically determine in real time) at least one further additional ergonomic support design element. More specifically, the ergonomic analysis application optionally receives data from the plurality of ergonomic sensors associated with the additional ergonomic support design element, transmits such data to a medical professional, receives from the medical professional an ergonomic evaluation, analyzes the ergonomic evaluation in order to determine a further additional ergonomic support design element, and facilitates printing of the further additional ergonomic support design element for the seat component associated with the first client. Accordingly, execution of the steps of the method 500 and repetition thereof reflect an iterative ergonomic support design analysis technique. Accordingly, the ergonomic analysis application is configured to facilitate printing of at least one additional ergonomic support design element based upon iterative analysis of medical professional ergonomic evaluation(s).

In an embodiment, the ergonomic analysis application transmits a recommendation to the first client that any additional ergonomic support design element(s) determined according to the method 400 or the method 500 supplant the initial ergonomic support design element. Alternatively, the ergonomic analysis application transmits a recommendation to the first client that any additional ergonomic design element(s) determined according to the method 400 or the method 500 be used in conjunction with the initial ergonomic support design element. According to such alternative, the ergonomic analysis application optionally recommends use of the initial ergonomic support design element at certain times and use of any additional ergonomic support design element(s) at other time(s) depending upon motive(s) of the first client with respect to the seat component. Recommending use of different ergonomic support design elements at different times may ensure ergonomic support in the event that the first client requires or prefers different posture positions for different activities. For instance, the ergonomic analysis application may recommend use of the initial ergonomic support design element during first client work periods but may recommend use of an additional ergonomic design element during first client entertainment periods.

In an alternative embodiment, the ergonomic analysis application incorporates aspects from both the method 400 and the method 500 in order to determine one or more additional ergonomic support design elements. According to such alternative embodiment, the ergonomic analysis application may determine an additional ergonomic support design element both through machine learning knowledge model analysis in accordance with step 415 of the method 400 and through analysis of an ergonomic evaluation received from a medical professional in accordance with step 520 of the method 500. In a further alternative embodiment, the ergonomic analysis application optionally executes steps from the method 400 to determine a first set of additional ergonomic support design elements and optionally executes steps from the method 500 to determine a second set of additional ergonomic support design elements.

In an example scenario in the context of the methods 200 and 400, Client A has ergonomic support issues throughout a typical workday while seated at his office chair and requests enhancement to his seat component via a client interface associated with a client ergonomic support application accessible through his mobile device. Client A submits responses to survey questions addressing his posture and subjective comfort level while seated in his office chair by accessing via the client interface a survey webpage including GUI control elements to facilitate replies. More specifically, Client A submits responses indicating lower back stiffness and upper back pain. According to step 215, an ergonomic analysis application of an ergonomic analysis server system receives the survey responses from Client A as well as any other available client-specific posture datapoints associated with Client A, such as available medical data from office visits, the results of mobile scans submitted by Client A, and any information regarding his office chair. According to step 220, the ergonomic analysis application analyzes, via a machine learning knowledge model constructed based upon a plurality of posture datapoints associated with multiple clients per steps 205 and 210, the client-specific posture datapoints associated with Client A in view of the plurality of posture datapoints associated with the multiple clients in order to select an initial ergonomic support design element for Client A. According to step 225, the ergonomic analysis application facilitates printing of the initial ergonomic support design element and further facilitates delivery thereof based upon a delivery request submitted by Client A through a webpage provided via the client interface.

As Client A uses the initial ergonomic support design element, a plurality of ergonomic sensors embedded in and otherwise associated with the initial ergonomic support design element record posture data, including data with respect to pressure points of contact between Client A and the initial ergonomic support design element. Upon expiration of a predefined evaluation period with respect to the initial ergonomic support design element, per step 230 the ergonomic analysis application provides an ergonomic refinement to Client A. More specifically, according to step 415, the ergonomic analysis application analyzes via the machine learning knowledge model data from the plurality of ergonomic sensors and updates to the plurality of posture datapoints received per steps 405 and 410 in order to determine an additional ergonomic support design element for Client A. More specifically, the ergonomic analysis application may determine based upon ergonomic sensors embedded at pressure points of contact that there is relatively more pressure applied by Client A with respect to the initial ergonomic design element at the left lower back than at the right lower back such that equal pressure is not applied by Client A at each of the pressure points of contact. Furthermore, based upon the updates to the plurality of posture datapoints, the ergonomic analysis application may determine that a different angle of curvature in the upper back area may better serve Client A, as the datapoints may indicate that the different angle of curvature is effective at assisting clients with upper back pain similar to the upper back pain of Client A. Consequently, according to step 420, the ergonomic analysis application facilitates printing of the additional ergonomic support design element in order to address issues detected by the ergonomic sensors, including the pressure point imbalance, and in order to account for the updates to the plurality of datapoints, including the newly determined angle of curvature information. Furthermore, the additional ergonomic support design element may address any comfort issues experienced by Client A consequent to use of the initial ergonomic support design element. The ergonomic analysis application may facilitate delivery of the additional ergonomic support design element based upon a delivery request submitted by Client A via the client interface. Optionally, to provide further iterative support for Client A, the ergonomic analysis application determines and facilitates printing of further additional ergonomic support design element(s) based upon further ergonomic sensor data and further updates to the plurality of posture datapoints.

In an example scenario in the context of the methods 200 and 500, Client B has ergonomic support issues while dining and working at her kitchen table and requests enhancement to her dining room chair via a client interface associated with a client ergonomic support application accessible through her laptop. Client B submits responses to survey questions addressing her posture and subjective comfort level while seated in her dining room chair by accessing via the client interface sensory elements that detect and process her vocal responses. According to step 215, an ergonomic analysis application of an ergonomic analysis server system receives the survey responses from Client B as well as any other available client-specific posture datapoints associated with Client B, such as available medical data from office visits, the results of mobile scans submitted by Client B, and any information regarding her dining room chair. According to step 220, the ergonomic analysis application analyzes, via a machine learning knowledge model constructed based upon a plurality of posture datapoints associated with multiple clients per steps 205 and 210, the client-specific posture datapoints associated with Client B in view of the plurality of posture datapoints associated with the multiple clients in order to select an initial ergonomic support design element for Client B. According to step 225, the ergonomic analysis application facilitates printing of the initial ergonomic support design element and further facilitates delivery thereof based upon a delivery request vocally submitted by Client B via the client interface.

As Client B uses the initial ergonomic support design element, a plurality of ergonomic sensors embedded in and otherwise associated with the initial ergonomic support design element record posture data, including data with respect to pressure points of contact between Client B and the initial ergonomic support design element. Upon determining that a spinal pressure metric as determined by sensor data exceeds a predefined spinal pressure threshold, per step 230 the ergonomic analysis application provides an ergonomic refinement to Client B. More specifically, according to step 510, the ergonomic analysis application transmits to an orthopedic specialist data from the plurality of ergonomic sensors received in accordance with step 505. Based upon the ergonomic sensor data, the orthopedic specialist may conclude that a spinal issue associated with Client B is not appropriately addressed through use of the initial ergonomic support design element. According to step 515, the ergonomic analysis application receives an ergonomic evaluation based upon the ergonomic sensor data. The ergonomic evaluation may include recommended design modifications to address the spinal issue. Furthermore, the ergonomic evaluation may take into account the subjective comfort level information submitted by Client B in response to the survey questions. According to step 520, the ergonomic analysis application analyzes the ergonomic evaluation in order to determine an additional ergonomic support design element for Client B. According to step 525, the ergonomic analysis application facilitates printing of the additional ergonomic support design element and further facilitates delivery thereof based upon a delivery request submitted by Client B via the client interface. Compared to the initial ergonomic support design element the additional ergonomic support design element includes improvements determined based upon the ergonomic evaluation. Furthermore, the additional ergonomic support design element may address any comfort issues experienced by Client B consequent to use of the initial ergonomic support design element. Optionally, to provide further iterative support for Client B, the ergonomic analysis application determines and facilitates printing of further additional ergonomic support design element(s) based upon further ergonomic evaluation(s) received from the orthopedic specialist and/or other professional(s) in view of further ergonomic sensor data.

The descriptions of the various embodiments of the present invention have been presented for purposes of illustration but are not intended to be exhaustive or limited to the embodiments disclosed. All kinds of modifications made to the described embodiments and equivalent arrangements should fall within the protected scope of the invention. Hence, the scope of the invention should be explained most widely according to the claims that follow in connection with the detailed description and should cover all possibly equivalent variations and equivalent arrangements. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method comprising:
constructing a machine learning knowledge model based upon a plurality of posture datapoints associated with multiple clients in order to identify a plurality of predefined ergonomic support design elements;
analyzing, via the machine learning knowledge model, client-specific posture datapoints associated with a first client in view of the plurality of posture datapoints in order to select an initial ergonomic support design element among the plurality of predefined ergonomic support design elements; and
facilitating printing of the initial ergonomic support design element for a seat component associated with the first client.

2. The computer-implemented method of claim 1, further comprising:
providing at least one ergonomic refinement to the first client based upon ergonomic sensor data.

3. The computer-implemented method of claim 2, further comprising:
responsive to detecting a change in posture of the first client via the ergonomic sensor data, notifying the first client of the change in posture via at least one alert.

4. The computer-implemented method of claim 2, wherein providing the at least one ergonomic refinement to the first client comprises:
analyzing, via the machine learning knowledge model, data from a plurality of ergonomic sensors associated with the initial ergonomic support design element and updates to the plurality of posture datapoints in order to determine an additional ergonomic support design element; and
facilitating printing of the additional ergonomic support design element for the seat component associated with the first client.

5. The computer-implemented method of claim 2, wherein providing the at least one ergonomic refinement to the first client comprises:
transmitting to a medical professional data from a plurality of ergonomic sensors associated with the initial ergonomic support design element;
receiving from the medical professional an ergonomic evaluation associated with the first client based upon the data from the plurality of ergonomic sensors;
analyzing the ergonomic evaluation in order to determine an additional ergonomic support design element; and
facilitating printing of the additional ergonomic support design element for the seat component associated with the first client.

6. The computer-implemented method of claim 1, wherein constructing the machine learning knowledge model comprises:
assigning to each client among the multiple clients a respective ergonomic support design category among a plurality of ergonomic support design categories;
facilitating printing of a respective test ergonomic support design element for each client among the multiple clients based upon the respective ergonomic support design category assigned to the client;
receiving evaluation data for each client among the multiple clients based upon sensor data collected from the respective test ergonomic support design element assigned to the client;
identifying one or more ergonomic patterns based upon analyzing the evaluation data in view of the plurality of posture datapoints;

training the machine learning knowledge model based upon the identified one or more ergonomic patterns; and defining the plurality of predefined ergonomic support design elements based upon the trained machine learning knowledge model.

7. The computer-implemented method of claim 1, wherein one or more of the client-specific posture datapoints associated with the first client comprises are based upon data from at least one weight sensor affixed to the seat component associated with the first client.

8. The computer-implemented method of claim 1, wherein facilitating printing of the initial ergonomic support design element for the seat component associated with the first client comprises facilitating printing of at least one armrest for the initial ergonomic support design element based upon measurements of the first client.

9. A computer program product comprising a computer readable storage medium having program instructions embodied therewith, the program instructions executable by a computing device to cause the computing device to:

construct a machine learning knowledge model based upon a plurality of posture datapoints associated with multiple clients in order to identify a plurality of predefined ergonomic support design elements;

analyze, via the machine learning knowledge model, client-specific posture datapoints associated with a first client in view of the plurality of posture datapoints in order to select an initial ergonomic support design element among the plurality of predefined ergonomic support design elements; and facilitate printing of the initial ergonomic support design element for a seat component associated with the first client.

10. The computer program product of claim 9, wherein the program instructions further cause the computing device to:

provide at least one ergonomic refinement to the first client based upon ergonomic sensor data.

11. The computer program product of claim 10, wherein the program instructions further cause the computing device to:

responsive to detecting a change in posture of the first client via the ergonomic sensor data, notify the first client of the change in posture via at least one alert.

12. The computer program product of claim 10, wherein providing the at least one ergonomic refinement to the first client comprises:

analyzing, via the machine learning knowledge model, data from a plurality of ergonomic sensors associated with the initial ergonomic support design element and updates to the plurality of posture datapoints in order to determine an additional ergonomic support design element; and facilitating printing of the additional ergonomic support design element for the seat component associated with the first client.

13. The computer program product of claim 10, wherein providing the at least one ergonomic refinement to the first client comprises:

transmitting to a medical professional data from a plurality of ergonomic sensors associated with the initial ergonomic support design element;

receiving from the medical professional an ergonomic evaluation associated with the first client based upon the data from the plurality of ergonomic sensors;

analyzing the ergonomic evaluation in order to determine an additional ergonomic support design element; and facilitating printing of the additional ergonomic support design element for the seat component associated with the first client.

14. The computer program product of claim 9, wherein constructing the machine learning knowledge model comprises:

assigning to each client among the multiple clients a respective ergonomic support design category among a plurality of ergonomic support design categories;

facilitating printing of a respective test ergonomic support design element for each client among the multiple clients based upon the respective ergonomic support design category assigned to the client;

receiving evaluation data for each client among the multiple clients based upon sensor data collected from the respective test ergonomic support design element assigned to the client;

identifying one or more ergonomic patterns based upon analyzing the evaluation data in view of the plurality of posture datapoints;

training the machine learning knowledge model based upon the identified one or more ergonomic patterns; and defining the plurality of predefined ergonomic support design elements based upon the trained machine learning knowledge model.

15. A system comprising:

a processor; and a memory storing an application program, which, when executed on the processor, performs an operation comprising:

constructing a machine learning knowledge model based upon a plurality of posture datapoints associated with multiple clients in order to identify a plurality of predefined ergonomic support design elements;

analyzing, via the machine learning knowledge model, client-specific posture datapoints associated with a first client in view of the plurality of posture datapoints in order to select an initial ergonomic support design element among the plurality of predefined ergonomic support design elements; and facilitating printing of the initial ergonomic support design element for a seat component associated with the first client.

16. The system of claim 15, wherein the operation further comprises:

providing at least one ergonomic refinement to the first client based upon ergonomic sensor data.

17. The system of claim 16, wherein the operation further comprises:

responsive to detecting a change in posture of the first client via the ergonomic sensor data, notifying the first client of the change in posture via at least one alert.

18. The system of claim 16, wherein providing the at least one ergonomic refinement to the first client comprises:

analyzing, via the machine learning knowledge model, data from a plurality of ergonomic sensors associated with the initial ergonomic support design element and updates to the plurality of posture datapoints in order to determine an additional ergonomic support design element; and facilitating printing of the additional ergonomic support design element for the seat component associated with the first client.

19. The system of claim 16, wherein providing the at least one ergonomic refinement to the first client comprises:
- transmitting to a medical professional data from a plurality of ergonomic sensors associated with the initial ergonomic support design element;
- receiving from the medical professional an ergonomic evaluation associated with the first client based upon the data from the plurality of ergonomic sensors;
- analyzing the ergonomic evaluation in order to determine an additional ergonomic support design element; and
- facilitating printing of the additional ergonomic support design element for the seat component associated with the first client.

20. The system of claim 15, wherein constructing the machine learning knowledge model comprises:
- assigning to each client among the multiple clients a respective ergonomic support design category among a plurality of ergonomic support design categories;
- facilitating printing of a respective test ergonomic support design element for each client among the multiple clients based upon the respective ergonomic support design category assigned to the client;
- receiving evaluation data for each client among the multiple clients based upon sensor data collected from the respective test ergonomic support design element assigned to the client;
- identifying one or more ergonomic patterns based upon analyzing the evaluation data in view of the plurality of posture datapoints;
- training the machine learning knowledge model based upon the identified one or more ergonomic patterns; and
- defining the plurality of predefined ergonomic support design elements based upon the trained machine learning knowledge model.

\* \* \* \* \*